(12) United States Patent
Hubiche et al.

(10) Patent No.: US 12,226,516 B2
(45) Date of Patent: Feb. 18, 2025

(54) HAIRCARE COMPOSITION COMPRISING MODIFIED VEGETABLE WAXES

(71) Applicant: GATTEFOSSÉ SAS, Saint-Priest (FR)

(72) Inventors: Vincent Hubiche, St Bonnet de Mure (FR); Jean-David Rodier, Villeurbanne (FR); Paula Lennon, Lyons (FR)

(73) Assignee: GATTEFOSSÉ SAS, Saint-Priest (FR)

( * ) Notice: Subject to any disclaimer, the term of this patent is extended or adjusted under 35 U.S.C. 154(b) by 633 days.

(21) Appl. No.: 17/047,222

(22) PCT Filed: Apr. 19, 2019

(86) PCT No.: PCT/FR2019/050935
§ 371 (c)(1),
(2) Date: Oct. 13, 2020

(87) PCT Pub. No.: WO2019/211544
PCT Pub. Date: Nov. 7, 2019

(65) Prior Publication Data
US 2021/0169772 A1 Jun. 10, 2021

(30) Foreign Application Priority Data
May 2, 2018 (FR) .................................. 1853765

(51) Int. Cl.
| | |
|---|---|
| *A61K 8/92* | (2006.01) |
| *A61K 8/34* | (2006.01) |
| *A61K 8/37* | (2006.01) |
| *A61Q 5/06* | (2006.01) |
| *A61Q 5/12* | (2006.01) |

(52) U.S. Cl.
CPC .............. *A61K 8/922* (2013.01); *A61K 8/345* (2013.01); *A61K 8/37* (2013.01); *A61Q 5/06* (2013.01); *A61Q 5/12* (2013.01)

(58) Field of Classification Search
None
See application file for complete search history.

(56) References Cited

U.S. PATENT DOCUMENTS

2008/0207778 A1* 8/2008 Rodier ................... A61Q 19/00
514/787
2015/0034116 A1 2/2015 Salese et al.

FOREIGN PATENT DOCUMENTS

| EP | 3031925 A1 * | 6/2016 | ............. A61K 8/062 |
|---|---|---|---|
| EP | 1933806 B1 | 8/2017 | |
| FR | 2760970 A1 | 9/1998 | |

OTHER PUBLICATIONS

Fatty Acid Synthesis and Modification, General Features of Fatty Acid Structure, https://web.archive.org/web/20070113030459/https://library.med.utah.edu/NetBiochem/FattyAcids/3_3.html (Year: 2007).*
Haihang Industry, Polyglycerol-3 Cas 56090-54-1, https://haihangchem.com/products/polyglycerol-3-cas-56090-54-1/ (Year: 2023).*
Freitas et al., Carnauba wax uses in food—A review, Food Chemistry 291 (2019) 38-48) (Year: 2019).*
Oseyko et al., Peculiarities of the lipid composition of sunflower wax, Ukrainian Journal of Food Science. 2021. vol. 236 9. Issue 2 (Year: 2021).*
International Search Report (and English translation) and Written Opinion of the International Searching Authority for International Application No. PCT/FR2019/050935 mailed on Jul. 18, 2019.
Anonymous, "Bulletin 22 Hydracire S—Jojoba Wax, Sunflower Wax & Mimosa Wax" Internet Article, Sep. 15, 2009, Retrieved from the Internet: http://alliance2u.co/pdf/Bulletin22.pdf [retrieved on Aug. 26, 2015] XP055209746, pp. 3-5.
Gattefossé, "ACTICIRE; 3 Waxes, 3 Benefits, 1 Ingredient", Apr. 16, 2013, Retrieved from the Internet: http://www.scsformulate.co.uk/wp-content/uploads/2015/08/Acticire-Brochure.pdf [retrieved on Jun. 10, 2016] XP055279702, Example; p. 11, p. 3.
Anonymous, "Moisturizing Hair Mask", Mar. 7, 2014, retrieved from www.gnpd.com, Abstract No. Database accession No. 2338412, Retrieved from: GNPD [online], MINTEL, XP055539088, abstract.

* cited by examiner

*Primary Examiner* — David J Blanchard
*Assistant Examiner* — Edwin Coleman Mitchell
(74) *Attorney, Agent, or Firm* — HESLIN ROTHENBERG FARLEY & MESITI P.C.

(57) ABSTRACT

A cosmetic hair care composition comprises a derivative of waxes obtained by the reaction of simultaneous transesterification of a mixture comprising jojoba wax and sunflower wax, in the presence of polyglycerol-3.

15 Claims, 4 Drawing Sheets

HAIRCARE COMPOSITION COMPRISING MODIFIED VEGETABLE WAXES

CROSS REFERENCE TO RELATED APPLICATIONS

This application is a national stage filing under section 371 of International Application No. PCT/FR2019/050935 filed on Apr. 19, 2019, and published on Nov. 7, 2019 as WO 2019/211544, which claims priority to French Application No. 1853765, filed on May 2, 2018. The entire contents of WO 2019/211544 are hereby incorporated herein by reference.

FIELD OF THE INVENTION

The invention relates to a hair care composition comprising a mixture of modified waxes, and its use.

PRIOR ART

Hair is constantly being exposed to difficult extrinsic conditions such as ultraviolet radiation, pollution moisture, chemical damage (cleaning, bleaching, perms), heat (hair dryers, straighteners, hair stylists, etc), or indeed to mechanical damage (combing etc).

Furthermore, the quantity of hair, like its quality, can decrease over time due to age and/or other factors such as insufficient cell renewal in the scalp, or in fact excessive or insufficient sebum production.

These various factors could lead to thinner and/or more fragile hair and/or could damage the visual appearance and/or feel of the hair.

As an example, in very humid conditions, the hair has a tendency to absorb water, which results in a loss of shape, makes it unruly, and causes the appearance of frizz. In contrast, under very dry conditions, the hair can dry out, become more fragile and have a less glossy appearance. Thus, it is important to strengthen the hydrophobic nature of the hair in order to limit the influence of environmental conditions.

In order to limit or prevent damage caused to hair, consumers look for hair care products, frequently known as conditioners, which can be used to protect the hair from external attack and improve its appearance.

These hair care products are principally constituted by silicone, vegetable oils and quaternary conditioners.

Silicones can be used to improve combing, introduce softness and produce a glossy appearance. However, it suffers from a number of disadvantages. They are synthetic products which are poorly biodegradable. Furthermore, they are hydrophobic and lipophobic compounds. As a consequence, they are more difficult to remove during cleaning by shampooing. Moreover, as it is used, silicones accumulate on the hair over time, making it heavier, which in particular impedes styling.

Vegetable oils and butters can partially replace silicones. They have the effect of nourishing the hair, hydrating it and softening it. However, these compounds tend to make the hair greasy and perform less well. On the other hand, vegetable oils and butters are unsaturated triglycerides which oxidize readily, which causes a problem as regards the stability of the formulations. In addition, in an emulsion type formulation, these oils are not easy to stabilize. For this reason, they are primarily used in the form of a liquid hair care oil.

Finally, quaternary conditioners or cationic polymers are intended to facilitate combing and combat static electricity by the positive charge they carry, which therefore neutralizes negative charges on the hair. However, these compounds could irritate the skin, are partially non-biodegradable and are definitely allergens.

To the knowledge of the Applicant, no hair care composition has been developed which does not suffer from the disadvantages mentioned above.

DETAILED DESCRIPTION OF THE INVENTION

The Applicant has entirely surprisingly discovered that the reaction product obtained from a mixture comprising jojoba wax, sunflower wax and polyglycerol-3 was beneficial as regards controlling the volume of the hair, controlling frizz, ease of combing, and improving the resistance to static electricity and the hydrophobic nature of the hair when it is used in hair care formulations, which may be wash-out or leave-in.

The term "frizz" designates hair which does not remain in shape in the styled hair, in other words "unruly" hair.

The Applicant's document EP 1 933 806 A1 describes a process for the preparation of an excipient by simultaneous mutual transformation of a solid wax and a liquid wax with a polyol. The mixture of jojoba wax, sunflower wax and polyglycerol-3 is not described.

The Applicant has established that it is possible to obtain a cosmetic composition, advantageously a hair care composition, comprising a derivative of waxes obtained by the reaction of simultaneous transesterification between jojoba wax and sunflower wax, in the presence of polyglycerol-3.

This hair care composition has equivalent or even superior effects on the hair without the disadvantages linked to the nature of the compounds of the prior art (non-biodegradable, difficult to clean, making the hair heavier, instability, or in fact crystallization of the formulation).

Thus, the present invention provides a hair care composition comprising a derivative of waxes obtained by the reaction of simultaneous transesterification of a mixture comprising jojoba wax and sunflower wax in the presence of polyglycerol-3.

Jojoba wax is a liquid with an oily, viscous, slightly yellowish appearance, which has a low odour, obtained by pressing *Simmondsia chinensis* seeds. Jojoba wax is essentially composed of unsaturated aliphatic monoesters containing 38 to 44 carbon atoms. These esters are constituted by linear unsaturated fatty acids and linear unsaturated fatty alcohols.

Sunflower wax constitutes a thin film around the seeds, i.e. the husk of the seed of the sunflower or *Helianthus annuus*. It is extracted from sunflower oil by filtration after a step for precipitation or "winterization". Thus, it is not sunflower oil, which is generally obtained pressure or solvent extraction from sunflower seeds In particular, sunflower wax does not have the same composition as sunflower oil, which is constituted by triglycerides. Sunflower wax is composed of saturated aliphatic monoesters containing 42 to 62 carbon atoms. These esters are constituted by linear saturated fatty acids and linear saturated fatty alcohols.

As an alternative to the non-hydrolysed form, the sunflower wax may furthermore be in a partially or completely hydrolysed form. In this case, linear saturated fatty acids and linear saturated fatty alcohols are employed. When using this wax, they will be recombined by the reaction of esterification with jojoba wax in the presence of polyglycerol-3.

The term "partially hydrolysed sunflower wax" designates between 50% and 100% hydrolysis of the sunflower wax, advantageously between 75% and 100%.

In the presence of polyglycerol-3, the mixture of jojoba wax and sunflower wax may furthermore optionally comprise at least one free or esterified saturated fatty alcohol, advantageously containing at least 22 carbon atoms, and/or a free or esterified saturated fatty acid, advantageously containing at least 22 carbon atoms.

Polyglycerol-3 is a polyol with formula $C_9H_{20}O_7$ and with a molar mass of approximately 240 g/mol. This compound carries an average of 5 alcohol functions (OH).

The Applicant has discovered that the product of the simultaneous reaction between jojoba wax, sunflower wax, which may optionally be partially or completely hydrolysed, in the presence of polyglycerol-3, is less hard than the product obtained from mixing the two waxes.

According to the Applicant, this behaviour may derive from the presence of novel polyol derivatives which do not exist when the products are mixed separately, as well as novel aliphatic esters. The polyol derivative corresponds to a structure in which all or a portion of the OH functions of the polyglycerol-3 have been esterified with linear saturated fatty acids of sunflower wax and linear unsaturated fatty acids of jojoba wax. Linear unsaturated fatty alcohols of jojoba wax and linear saturated fatty alcohols of sunflower wax are then liberated during this reaction. The novel aliphatic esters are constituted by linear unsaturated fatty acids of jojoba wax combined with the linear saturated fatty alcohols of sunflower wax and linear saturated fatty acids of sunflower wax combined with linear unsaturated fatty alcohols of jojoba wax.

A random redistribution of the acids and alcohols composing the waxes is obtained by means of this transesterification reaction. Thus, at the end of the reaction, the derivative of waxes contains esters of mono-unsaturated or linear saturated acids and linear saturated alcohols, esters of linear saturated acids and linear mono-unsaturated or saturated alcohols, free linear saturated alcohols, free linear mono-unsaturated or saturated alcohols and the polyol esters described above, in addition to the initial constituents which have not reacted.

Advantageously, the weight ratio of jojoba wax/sunflower wax represents between 50/50 and 90/10, advantageously between 60/40 and 80/20, preferably 70/30.

Preferably, the weight ratio of jojoba wax and sunflower wax/polyglycerol-3 represents between 99/1 and 80/20, advantageously between 98/2 and 90/10, preferably 95/5.

In accordance with one embodiment of the invention, the derivative of waxes, obtained by the reaction of simultaneous transesterification of a mixture comprising jojoba wax, sunflower wax in the presence of polyglycerol-3, represents between 0.01% and 20% by weight of the composition, advantageously between 0.1% and 5%.

The derivative of waxes obtained using the transesterification reaction mentioned above has oil-in-water emulsification behaviour, as well as a capacity for absorbing water.

In accordance with the present invention, the derivative of waxes is obtained by the reaction of simultaneous transesterification of a mixture comprising jojoba wax and sunflower wax in the presence of polyglycerol-3 and at least one catalyst.

The at least one catalyst is selected from the group comprising hydroxides, alkaline alkoxides and alkaline earths.

Advantageously, the at least one catalyst is selected from the group comprising sodium hydroxide, potassium hydroxide (in alcoholic or aqueous solution, or in the solid form), calcium hydroxide, potassium carbonate or sodium carbonate.

In practice, the reaction is carried out at a temperature in the range 150° C. to 240° C., advantageously in the range 180° C. to 220° C.

The invention also concerns the hair care composition as defined above, for use for:
controlling the volume of hair;
an anti-frizz effect;
untangling hair, advantageously in order to facilitate combing;
improving the definition and hold of curls in the hair;
counteracting static electricity generated in the hair; and
increasing the hydrophobic nature of hair.

The hair care composition comprising the derivative of waxes in accordance with the invention may be formulated into any of the galenical forms which are normally used for hair care application, in particular, for example, in the anhydrous form, in the form of an oil-in-water emulsion, a water-in-oil emulsion, a multiple emulsion, a microemulsion, a nanoemulsion, a gel or a hydro-alcoholic solution.

This composition may be fluid to a greater or lesser extent and in the form of a cream, an ointment, a milk, a lotion, a solution, a serum, a conditioner, a hair care product, a wax, a mask or a gel.

Furthermore, the hair care composition comprising the derivative of waxes in accordance with the invention is for application to the hair and to other types of body hair, in this case the beard, moustache, eyelashes or eyebrows.

The hair care composition may also comprise excipients which are in normal use in the hair care field, such as fats, detergent and/or conditioning surfactants, emulsification and co-emulsification agents, hydrophilic or lipophilic gelling agents, preservatives, antioxidants, solvents, exfoliating agents, fragrances, fillers, hydrophilic and lipophilic sun screens, colorants, neutralizing agents, pro-penetrating agents, and polymers. These types of excipients are well known to the person skilled in the art.

In practice, the quantities of these various excipients are those which are conventionally used in the fields under consideration, and the sum of the excipients is preferably 0.01% to 99.9% of the total weight of the composition.

Appropriate fats which may be cited are mineral oils, oils of animal origin (such as lanolin), vegetable oils and butters, synthesized oils (such as hydrogenated polydecenes, for example), ethers (such as dicaprylic ether, for example), esters (such as octyldodecyl myristate, isopropyl palmitate, triglyceryl caprylocaprate, for example) and fluorinated oils. Fatty alcohols, fatty acids and gums may be used as the fats.

Examples of appropriate detergent and/or conditioning surfactants which may be cited are non-ionic, anionic, cationic or amphoteric surfactants and their mixtures such as, for example, alkyl sulphates, alkylether sulphates such as sodium lauryl ether sulphate, alkyl betaines such as cocamidopropyl betaine, or quaternary ammonium salts.

Examples of appropriate emulsification agents and co-emulsification agents which may be cited are sucrose and fatty acid esters, sorbitan and fatty acid esters, fatty acid and oxyethylenated sorbitan esters, fatty alcohol and polyethylene glycol ethers, glycerol and fatty acid esters, alkyl sulphates, alkyl ether sulphates, alkyl phosphates, alkyl polyglucosides, and dimethicone copolyols.

Examples of appropriate hydrophilic gelling agents which may be cited are carboxyvinylic polymers (carbomers), acrylic copolymers such as acrylate/alkylacrylate copolymers, polyacrylamides, polysaccharides such as xanthan gum, guar gum, natural gums such as cellulose gum and derivatives, starches and their derivatives, clays and 2-acrylamido-2-methylpropane copolymers.

Examples of appropriate lipophilic gelling agents which may be cited are modified clays such as bentones, metal salts of fatty acids, hydrophobic silica and ethylcellulose.

Examples of appropriate preservatives which may be cited are benzoic, sorbic, propionic, salicylic, dehydroacetic acids and their salts, benzyl alcohol, ethylhexyl glycerin, parabens, their salts and esters, triclosan, imidazolidinyl urea, 5-phenoxyethanol, dimethylol dimethyl (DMDM) hydantoin, diazolidinyl urea, and chlorphenesin.

Examples of appropriate antioxidants which may be cited are chelating agents such as ethylene diamine tetraacetic acid (EDTA) and its salts, sodium metabisulphite, salicylic, ascorbic and citric acids and their salts, sodium tartrate, sodium gluconate, carotenoids and tocopherols.

Examples of solvents which may be used in the hair care composition (distinct from the extraction solvent) which may be cited are water, advantageously demineralized water, ethanol, glycerin, propylene glycol, propanediol, butylene glycol, and sorbitol.

Examples of appropriate exfoliating agents which may be cited are chemical exfoliating agents such as alpha-hydroxylated acids (AHA), and physical exfoliating agents such as natural or synthetic powders.

Examples of appropriate fillers which may be cited are talc, kaolin, mica, sericite, magnesium carbonate, aluminium silicate, magnesium silicate, and organic powders such as nylon.

Examples of appropriate colorants which may be cited are lipophilic colorants, hydrophilic colorants, pigments and nacres which are in normal use in hair care compositions, and their mixtures.

Appropriate neutralising agents which may be cited are sodium hydroxide, triethanolamine, aminomethyl propanol, and potassium hydroxide.

Examples of appropriate pro-penetrating agents which may be cited are alcohols and glycols (ethanol, propylene glycol), ethoxydiglycol, alcohols and fatty acids (oleic acid), fatty acid esters, and dimethyl isosorbide.

In addition to the functional compound in accordance with the invention, in this case the derivative of waxes, the composition of the invention may also contain active ingredients. Examples of appropriate active ingredients which may be cited are anti-dandruff active ingredients, decolorizing agents, restructuring agents, thermal protection agents, radical scavengers and more generally antioxidants, emollients, moisturizers, anti-seborrheic agents, anti-inflammatories, keratolytic and/or desquamating agents, draining agents, anti-irritants, soothing agents, vitamins and their mixtures, mattifying agents and agents producing gloss, healing agents, antiseptics, essential oils and proteins such as keratin.

The manner of implementation of the invention and the advantages thereof will become more apparent from the following exemplary embodiments, given by way of non-limiting indication and with reference to the accompanying figures.

FIGURES

EXAMPLES OF EMBODIMENTS OF THE INVENTION

Figure 1:
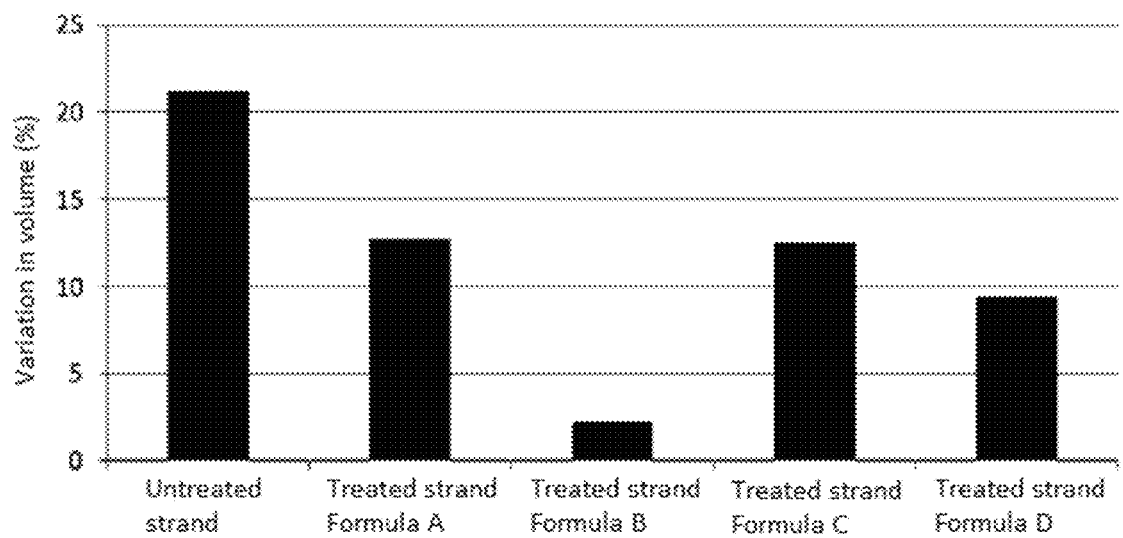
FIG. 1 represents the variation in the volume of hair, as a percentage, for different formulations.

Example 1: Obtaining a Derivative of Waxes

The derivative of waxes was obtained by the simultaneous transesterification of non-hydrolysed jojoba wax and sunflower wax, in the presence of polyglycerol-3.
Composition of Initial Reaction Mixture:

| Jojoba wax | 300 g |
| Sunflower wax (non-hydrolysed) | 177 g |
| Polyglycerol-3 | 22 g |
| Sodium hydroxide | 1 g |

The substances were introduced into a one litre stirred reactor. The reaction was carried out at 210° C. for 12 hours, with nitrogen inerting. At the end of the constant temperature stage, the catalyst was neutralized. The derivative of waxes was recovered after having separated a portion of the unreacted polyglycerol, then filtered in order to eliminate the neutralizing salts. The quantity of derivative of waxes which was recovered was approximately 475 g. The product obtained was beige in colour and had a soft consistency. The hydroxyl index was approximately 33 mg KOH/g and the dropping point was 62° C.

Example 2: Obtaining a Derivative of Waxes

The derivative of waxes was obtained by the simultaneous transesterification of jojoba wax and partially hydrolysed sunflower wax, in the presence of polyglycerol-3.
Composition of Initial Reaction Mixture:

| Jojoba wax | 301 g |
| Sunflower wax, 82% hydrolysed | 174 g |
| Polyglycerol-3 | 22 g |
| Sodium hydroxide | 0.5 g |

The substances were introduced into a one litre stirred reactor. The reaction was carried out at 215° C., for 6 hours, with nitrogen inerting. The acid index of the reaction mixture was 24 mg KOH/g. At the end of the constant temperature stage, the acid index was 0.5 mg KOH/g. The catalyst was neutralized. The derivative of waxes was recovered, after having separated a portion of the unreacted polyglycerol, then filtered in order to eliminate the neutralizing salts. The quantity of derivative of waxes which was recovered was approximately 488 g. The product obtained was brown in colour marron and had a harder consistency than that of Example 1. The dropping point which was measured was 66.1° C.

Example 3: Obtaining a Derivative of Waxes

The derivative of waxes was obtained by the simultaneous transesterification of jojoba wax and non-hydrolysed sunflower wax, in the presence of polyglycerol-3 and long chain linear saturated acids and fatty alcohols.
Composition of Initial Reaction Mixture:

| | |
|---|---|
| Jojoba wax | 305 g |
| Sunflower wax (non-hydrolysed) | 135 g |
| Behenic acid (C22) | 21 g |
| Behenyl alcohol (C22) | 21 g |
| Polyglycerol-3 | 17 g |
| Sodium hydroxide | 1 g |

The substances were introduced into a one litre stirred reactor. The reaction was carried out at 215° C., for 12 hours, with nitrogen inerting. At the end of the constant temperature stage, the acid index was 0.1 mg KOH/g. The catalyst was neutralized. The derivative of waxes was recovered then filtered in order to eliminate the neutralizing salts. The quantity of derivative of waxes which was recovered was approximately 490 g. The product obtained was pale yellow in colour and had a soft consistency. The dropping point which was measured was 62.1° C. and the hydroxyl index was 42 mg KOH/g.

Example 4: Test Formulations

| Name of ingredient | INCI name | Formula A | Formula B | Formula C | Formula D |
|---|---|---|---|---|---|
| | | % ingredient | | | |
| Demineralized water | Water | 88.3 | 86.3 | 86.3 | 86.3 |
| Emulium ® Delta | Cetyl alcohol, Glyceryl stearate, PEG-75 stearate, Ceteth-20, Steareth-20 | 6.0 | 6.0 | 6.0 | 6.0 |
| Derivative of waxes of Example 3 | | — | 2.0 | — | — |
| Silicone oils | Dimethicone, Dimethiconol | — | — | 2.0 | — |
| Quaternary ammonium compounds | Behentrimonium chloride | — | — | — | 2.0 |
| Mineral oil AAB2 | Mineral oil | 3.0 | 3.0 | 3.0 | 3.0 |
| Schercemol ™ dis ester | Diisopropyl sebacate | 2.0 | 2.0 | 2.0 | 2.0 |
| PE 9010 | Phenoxyethanol, Ethylhexyl glycerin | 0.7 | 0.7 | 0.7 | 0.7 |
| TOTAL | | 100 | 100 | 100 | 100 |

Formula A corresponded to a placebo formula, formula B contained the derivative of waxes in accordance with the invention, formula C contained silicones and formula D contained quaternaries.

Example 5: Measurement of Hair Volume

With the aid of the Rumba instrument from Bossa Nova Technologie, dedicated to the in vitro measurement of the orientation of hair fibres, the variation in volume of a strand of decolorized hair (curled brown hair) and treated with a formula (0.5 g of formula per 1 g of hair) when it had been stored for 4 h in humid conditions (30° C./>75% RH) was measured.

The results are shown in FIG. 1.

TABLE 1

Measurement of the variation in volume of a strand of hair

| | Variation in volume (%) |
|---|---|
| Untreated strand | +21.2 |
| Strand treated with Formula A (placebo) | +12.7 |
| Strand treated with Formula B (derivative of waxes of Example 3) | +2.2 |
| Strand treated with Formula C (silicones) | +12.5 |
| Strand treated with Formula D (quaternaries) | +9.4 |

In humid conditions, an untreated strand of hair has a tendency to swell because of the formation of hydrogen bridges between the fibres due to the presence of water (+21.2%). Application of formula B, containing 2% of the derivative of waxes of Example 3, enabled this swelling to be drastically reduced (+2.2%), far more than formula A, the placebo, (+12.7%), that containing silicones, formula C, (+12.5%) and that containing quaternaries, formula D (+9.4%).

Example 6: Measurement of Anti-Frizz Effect

With the aid of the Rumba instrument from Bossa Nova Technologie, the appearance of frizz was measured after washing with a standard shampoo and application to a decolorized strand of hair (curly brown hair) of a formula (0.5 g of formula per 1 g of hair) then following storage for 1 h under standardised conditions (23° C./50% relative humidity; RH).

Figure 2:
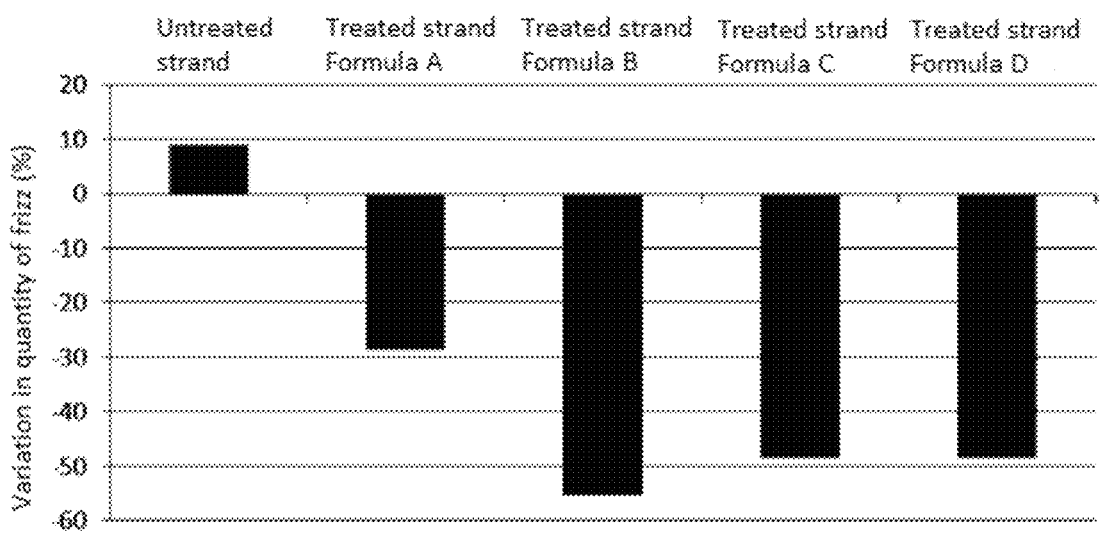
FIG. 2 represents the variation in the amount of frizz, as a percentage, for different formulations.

The results are shown in FIG. 2.

TABLE 2

Measurement of the variation in frizz frequency

| | Variation in frizz (%) |
|---|---|
| Untreated strand | +8.8 |
| Strand treated with Formula A (placebo) | −28.7 |
| Strand treated with Formula B (derivative of waxes of Example 3) | −55.3 |
| Strand treated with Formula C (silicones) | −48.3 |
| Strand treated with Formula D (quaternaries) | −48.5 |

Under standardised conditions (slightly dry atmosphere), a strand of hair which had been washed but not then treated will have a tendency to continue to form frizz (+8.8%). Application of formula B, containing 2% of the derivative of waxes of Example 3, enabled the quantity of frizz formed following shampooing to be reduced (−55.3%), far more effectively than with formula A, the placebo, (−28.7%), and with a performance equivalent to formula C, containing silicones, (−48.3%) and to formula D, containing quaternaries (−48.5%).

Example 7: Measurement of Combability

With the aid of a TA.XTPlus texturometer from Texture Technologies equipped with a combing system, the force necessary to comb a decolorized strand of hair (brown curls) before and after treatment of the strand with a formula (0.5 g of formula per 1 g of hair) was measured. After treatment, each strand was stored for 30 minutes at 23° C./50% RH before the measurement, in order to allow it to dry.

Figure 3:
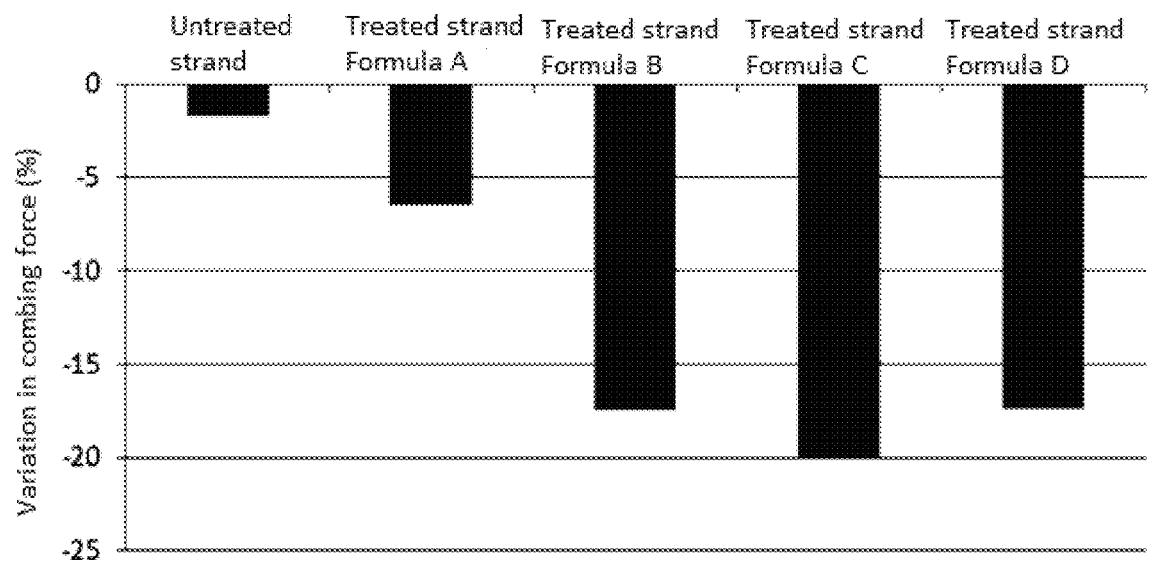
FIG. 3 represents the variation in the hair combing force, as a percentage, for different formulations.

The results are shown in FIG. 3.

TABLE 3

Measurement of the variation in combing force

| | Variation in combing force (%) |
|---|---|
| Untreated strand | −1.7 |
| Strand treated with Formula A (placebo) | −6.5 |
| Strand treated with Formula B (derivative of waxes of Example 3) | −17.5 |
| Strand treated with Formula C (silicones) | −20.1 |
| Strand treated with Formula D (quaternaries) | −17.3 |

The strand treated with formula B, containing the derivative of waxes of Example 3, exhibited better ease of combing (−17.5%), i.e. a smaller force was necessary in order to comb the strand. In contrast, formula B, the placebo, exhibited a smaller reduction (−6.5%). The performance obtained with the formula in accordance with the invention was equivalent to that obtained with formula D, containing quaternaries, (−17.3%) and close to that for formula C, containing silicones (−20.1%).

Example 8: Measurement of Curl Hold

Strands of hair (standard brown) were decolorized then washed before being treated with a formula (0.5 g of formula per 1 g of hair) for 3 minutes then rinsed with water. The strands were then placed on rollers and allowed to dry for 24 h under dry conditions (23° C./30% RH). After drying, the rollers were removed, and the size of the strand was measured before then after storage for 4 h under humid conditions (34° C./55% HR).

Figure 4:
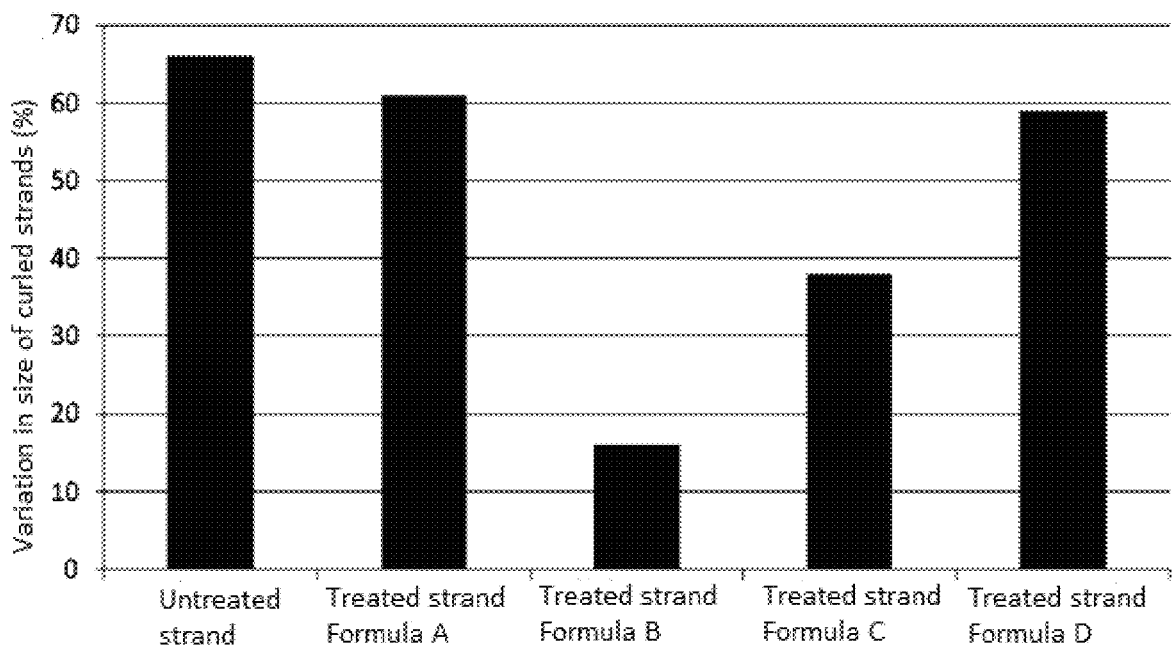
FIG. 4 represents the variation in the size of strands of curled hair, as a percentage, for different formulations.

The results are shown in FIG. 4.

TABLE 4

Measurement of the variation in the size of curled strands

| | Variation in size of curled strands |
|---|---|
| Untreated strand | +66% |
| Strand treated with Formula A (placebo) | +61% |
| Strand treated with Formula B (derivative of waxes of Example 3) | +16% |
| Strand treated with Formula C (silicones) | +38% |
| Strand treated with Formula D (quaternaries) | +59% |

While an untreated curled strand had become a great deal longer after 4 h (+66%), the strand treated with formula B, containing the derivative of waxes of Example 3, was only slightly deformed (+16%). Formula A, the placebo, had practically no effect (+61%), as was the case with formula D, containing quaternaries, (+59%). Finally, formula C, containing silicones, exhibited a mediocre performance (+38%).

Example 9: Measurement of the Resistance to Static Electricity

Strands of hair (standard brown) were washed before being treated with formula (0.5 g of formula per 1 g of hair) for 3 minutes then rinsed with water. The strands were then placed under dry conditions for 24 h (23° C./30% RH). After drying, an inflated balloon was passed over the strand and back twice in order to generate static electricity (simulating very dry air, a regular occurrence in winter). Next, the appearance of each strand was evaluated visually.

The static electricity generated on the hair brought about repulsion between the fibres which had been charged.

Figure 5:
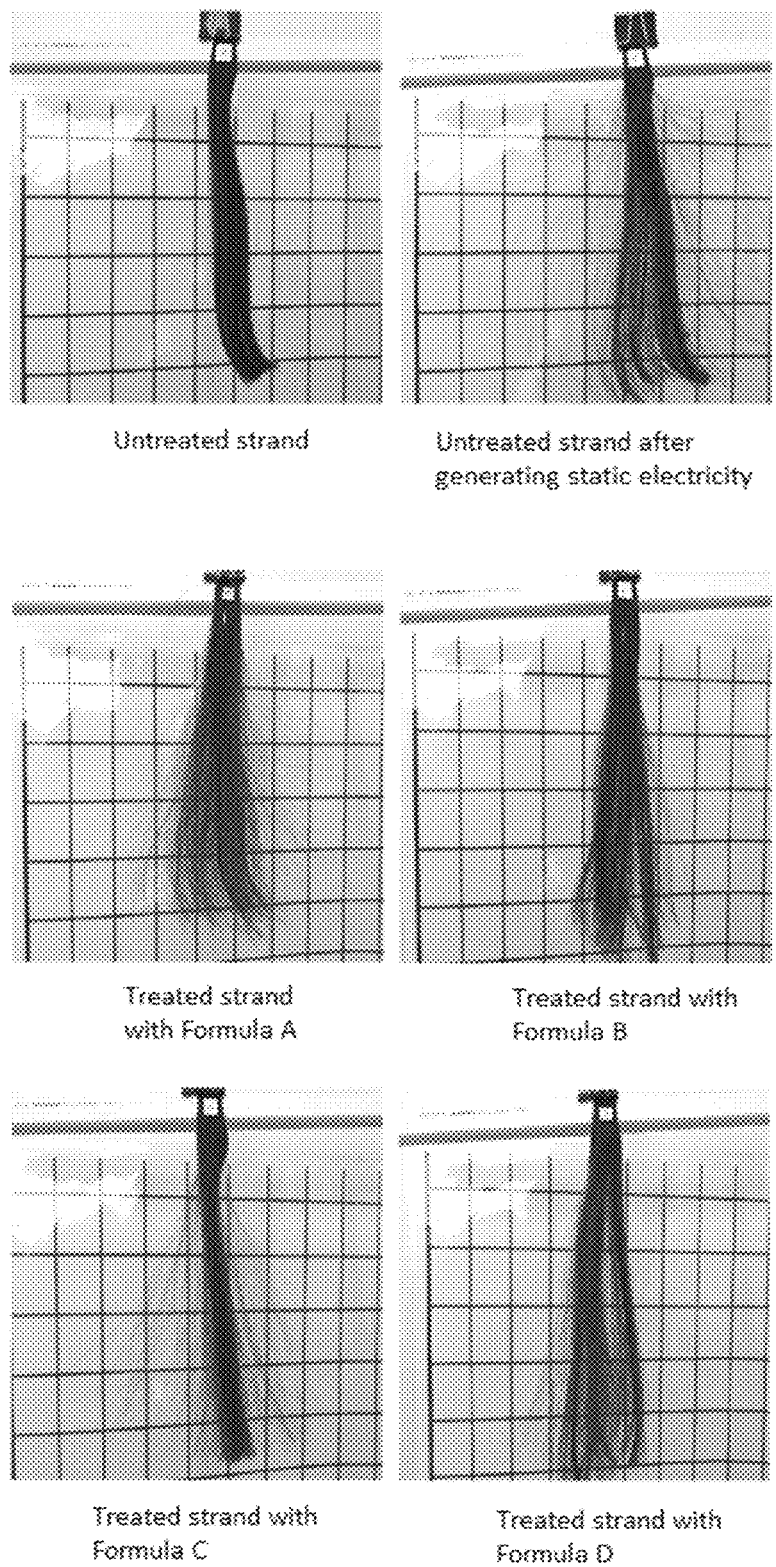
FIG. 5 represents the variation in the resistance to static electricity for different formulations.

The results are shown in FIG. 5.

Application of formula B, containing the derivative of waxes of Example 3, enabled the capacity of the hair to become electrically charged to be limited, and therefore to be smoothed. The performance obtained was equivalent to that obtained with formula D, containing quaternaries. Formulation C, containing silicones, had no effect on the static electricity.

Example 10: Measurement of Hydrophobicity i) Demineralized Water

In order to quantify the hydrophobicity provided by the derivative of waxes of Example 3, the various formulae were applied to a glass slide with the aid of a 30 μm drag ruler ("Bird/Baker dumb-bell coating applicator") then allowed to dry for 3 h under dry conditions (23° C./30% RH). With the aid of an ILMS goniometer from GBX Instruments, a drop of demineralized water was deposited on the surface and the contact angle of the drop of water was measured, knowing that the bigger it is, the more hydrophobic is the support.

The term "demineralized water" designates water which is free from minerals and polluting particles.

Formula A, the placebo, produced a contact angle of 62° and formula C, containing silicones, produced a contact angle of 57°, equivalent to the placebo. Formula D, containing quaternaries (highly hydrophilic), produced an angle of 27°. Finally, formula B, containing the derivative of waxes in accordance with Example 3, produced a contact angle of 85°, demonstrating the increase in the hydrophobicity provided by using the derivative of waxes of Example 3.

ii) Polluted Water

In order to quantify the importance of the derivative of waxes in accordance with the invention in reducing contact and adhesion of pollutants to hair, a test in accordance with the protocol of Example 10i) was used and a polluted drop of water was deposited on the surface of the glass slide.

The term "polluted water" designates water containing particles of pollution collected in an urban atmosphere (Urban dust NIST1649B; Sigma-Aldrich).

The results demonstrate a similar tendency to that observed with a drop of demineralized water, namely that a higher hydrophobicity is provided by using the derivative of waxes of Example 3 compared with the other formulae that were tested.

Example 11: Comparison of the Visual Appearance of a Derivative of Waxes in Accordance with the Invention Compared with a Prior Art Derivative of Waxes The formulation for the derivative of waxes in accordance with the invention was that of Example 3.

The formulation of the derivative of waxes in accordance with the prior art had the following initial composition for the reaction mixture:

| | |
|---|---|
| Jojoba wax | 571 g |
| Candellila wax | 123 g |
| Rice wax | 122 g |
| Polyglycerol-3 | 144 g |
| Potassium carbonate | 40 g |

Figure 6:
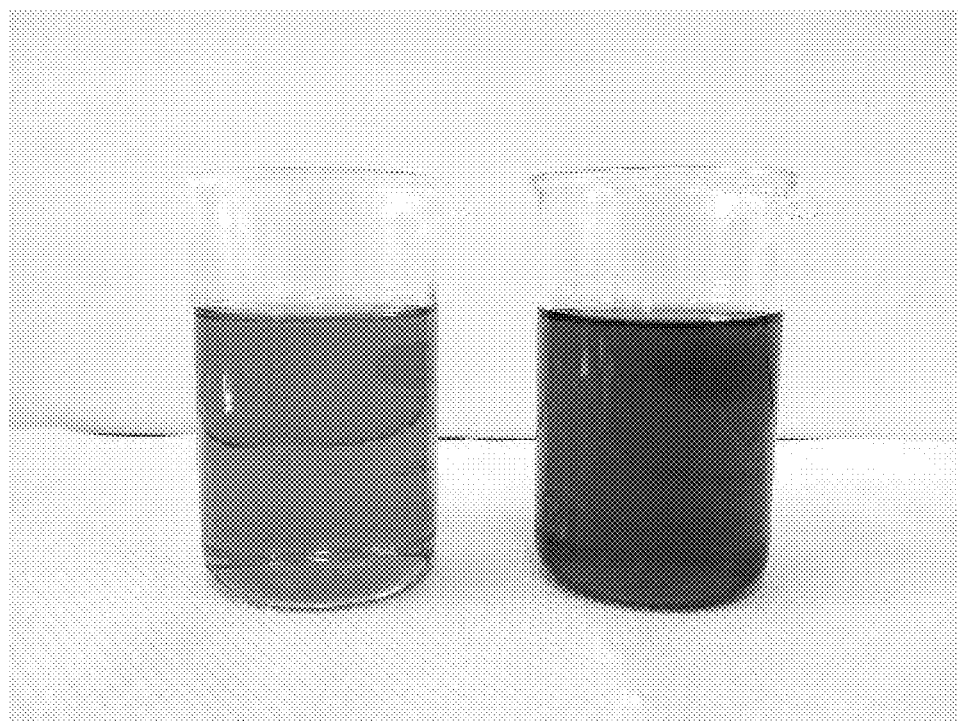
FIG. 6 represents a comparison of liquid forms at 80° C. of a derivative of waxes in accordance with the invention (left hand beaker) with a prior art derivative of waxes (right hand beaker)

The derivative of waxes in the liquid form at 80° C. are shown in FIG. 6.

The derivative in accordance with the invention, obtained from jojoba wax and sunflower wax in the presence of polyglycerol-3, was far less coloured (FIG. 6, left hand beaker) than the prior art derivative obtained from jojoba wax, rice wax and candelilla wax in the presence of polyglycerol-3 (FIG. 6, right hand beaker).

According to the Applicant, rice wax and candelilla wax become coloured during the synthesis and the resulting derivative then colours formulations using this derivative of waxes, which is impossible to mask if the formulator does not use other colouring ingredients such as pigments. The aesthetic qualities of the final product are thus deleteriously affected.

This aesthetic alteration to the hair product is not observed when using the formulation for the derivative of waxes in accordance with the invention.

Example 12: Examples of Formulae

Moisturizing night cream for hair

| INCI name | Matter, % |
|---|---|
| WATER | 55.56 |
| GLYCERIN | 6.00 |
| INULIN | 1.50 |
| CYAMOPSIS TETRAGONOLOBA GUM | 1.30 |
| MICROCRYSTALLINE CELLULOSE, CELLULOSE GUM | 1.00 |
| WATER | 4.00 |
| SODIUM STEAROYL GLUTAMATE | 0.20 |
| POLYGLYCERYL-6 DISTEARATE, JOJOBA ESTERS, POLYGLYCERYL-3 BEESWAX, CETYL ALCOHOL | 2.50 |
| CRAMBE ABYSSINICA SEED OIL | 5.00 |
| Derivative of waxes of Example 3 | 2.50 |
| C10-18 TRIGLYCERIDES | 4.00 |
| OCTYLDODECYL MYRISTATE | 3.00 |
| MANGIFERA INDICA (MANGO) SEED BUTTER | 2.00 |
| HYDROGENATED ETHYLHEXYL OLIVATE, HYDROGENATED OLIVE OIL UNSAPONIFIABLES | 2.00 |
| TOCOPHEROL | 0.04 |
| WATER, MANGIFERA INDICA (MANGO) FRUIT EXTRACT | 3.00 |
| DMDM HYDANTOIN, IODOPROPYNYL BUTYL-CARBAMATE | 0.40 |
| HYDROLYZED SOY PROTEIN | 5.00 |
| PARFUM | 1.00 |
| TOTAL | 100 |

Strengthening hair mask

| INCI name | Matter, % |
|---|---|
| WATER | 64.6 |
| MICROCRYSTALLINE CELLULOSE, CELLULOSE GUM | 2.5 |
| GLYCERIN | 2.0 |
| XANTHAN GUM | 0.3 |
| INULIN | 2.5 |
| SODIUM STEAROYL GLUTAMATE | 0.3 |
| WATER | 10.0 |
| POLYGLYCERYL-6 DISTEARATE | 1.5 |
| GLYCERYL STEARATE | 1.5 |
| CETYL ALCOHOL | 1.0 |
| C10-18 TRIGLYCERIDES | 1.0 |
| THEOBROMA CACAO (COCOA) SEED BUTTER | 2.0 |
| Derivative of waxes of Example 3 | 2.0 |
| CANDELILLA (EUPHORBIA CERIFERA) WAX | 0.7 |
| OCTYLDODECYL MYRISTATE | 2.0 |
| PHENOXYETHANOL, ETHYLHEXYLGLYCERIN | 0.8 |
| PARFUM | 0.3 |
| HYDROGLYCOLIC EXTRACT OF PLANT(S) | 3.0 |
| HYDROLYZED SOY PROTEIN | 2.0 |
| TOTAL | 100 |

Styling wax

| INCI name | Matter, % |
|---|---|
| WATER | 65.2 |
| GLYCERIN | 7.0 |
| TAPIOCA STARCH | 2.0 |
| SODIUM POLYACRYLATE | 1.0 |
| POLYGLYCERYL-6 DISTEARATE, JOJOBA ESTERS, POLYGLYCERYL-3 BEESWAX, CETYL ALCOHOL | 4.0 |
| BEESWAX | 14.0 |
| Derivative of waxes of Example 3 | 5.5 |
| PHENOXYETHANOL, ETHYLHEXYLGLYCERIN | 0.8 |
| PARFUM | 0.5 |
| TOTAL | 100 |

Anti-frizz hair care

| INCI name | Matter, % |
|---|---|
| WATER | 71.0 |
| INULIN | 2.0 |
| SCLEROTIUM GUM | 0.5 |
| POLYGLYCERYL-6 DISTEARATE, JOJOBA ESTERS, POLYGLYCERYL-3 BEESWAX, CETYL ALCOHOL | 3.0 |
| Derivative of waxes of Example 3 | 2.0 |
| COCO-CAPRYLATE | 20.0 |
| PHENOXYETHANOL, ETHYLHEXYLGLYCERIN | 1.0 |
| PARFUM | 0.3 |
| WATER, YELLOW 5 | 0.2 |
| TOTAL | 100 |

Beard conditioner

| INCI name | Matter, % |
|---|---|
| POLYGLYCERYL-6 DISTEARATE, JOJOBA ESTERS, POLYGLYCERYL-3 BEESWAX, CETYL ALCOHOL | 3.00 |
| STEARYL HEPTANOATE, STEARYL CAPRYLATE | 7.00 |
| CAMELLIA JAPONICA SEED OIL | 10.00 |
| SIMMONDSIA CHINENSIS (JOJOBA) SEED OIL | 7.00 |
| Derivative of waxes of Example 3 | 3.50 |
| CETYL ALCOHOL | 1.50 |
| TOCOPHEROL | 0.05 |
| PHENOXYETHANOL, ETHYLHEXYLGLYCERIN | 1.00 |
| WATER | 59.05 |
| GLYCERIN | 6.00 |

-continued

Beard conditioner

| INCI name | Matter, % |
|---|---|
| MICROCRYSTALLINE CELLULOSE, CELLULOSE GUM | 1.00 |
| XANTHAN GUM | 0.20 |
| PARFUM | 0.50 |
| PROPANEDIOL, WATER, *HORDEUM VULGARE* SEED EXTRACT | 0.20 |
| TOTAL | 100 |

The invention claimed is:

1. A method for improving hair comprising applying to the hair a cosmetic hair care composition comprising a derivative of waxes obtained by the reaction of simultaneous transesterification of a mixture comprising (a) jojoba wax, (b) non-hydrolyzed sunflower wax, (c) behenyl alcohol, and (d) behenic acid, said reaction being carried out at a temperature in the range 150° C. to 240° C. and in the presence of polyglycerol-3, wherein components (a)-(d) are present in an initial reaction mixture upon which the said simultaneous transesterification is performed.

2. The method as claimed in claim 1, wherein the weight ratio of jojoba wax/sunflower wax present in the reaction forming the derivative of waxes in the cosmetic hair care composition represents between 50/50 and 90/10.

3. The method as claimed in claim 1, wherein the weight ratio of jojoba wax and sunflower wax/polyglycerol-3 present in the reaction forming the derivative of waxes in the cosmetic hair care composition represents between 99/1 and 80/20.

4. The method as claimed in claim 1, wherein the derivative of waxes in the cosmetic hair care composition represents between 0.01% and 20% by weight of the composition.

5. The method as claimed in claim 1, wherein the reaction is carried out in the presence of at least one catalyst, and wherein catalysts used in the invention consist of one or more chemical catalysts.

6. The method as claimed in claim 5, wherein the one or more chemical catalysts are selected from hydroxide catalysts, alkaline alkoxide catalysts and alkaline earth catalysts.

7. The method as claimed in claim 1, wherein the method for improving hair comprises untangling hair.

8. The method as claimed in claim 1, wherein the method for improving hair comprises improving the definition and hold of curls in hair.

9. The method as claimed in claim 1, wherein the method for improving hair comprises controlling hair volume, reducing frizz, or counteracting static electricity generated in hair.

10. The method as claimed in claim 1, wherein the method for improving hair comprises increasing the hydrophobic nature of hair.

11. The method as claimed in claim 2, wherein the weight ratio of jojoba wax/sunflower wax represents between 60/40 and 80/20.

12. The method as claimed in claim 3, wherein the weight ratio of jojoba wax and sunflower wax/polyglycerol-3 represents between 98/2 and 90/10.

13. The method as claimed in claim 4, wherein the derivative of waxes represents between 0.1% and 5% by weight of the composition.

14. The method as claimed in claim 1, wherein, in said mixture, the (c) behenyl alcohol and the (d) behenic acid are each present in an amount that represents 4.2 wt %, based on the total weight of components (a)-(d) and the polyglycerol-3 in the mixture.

15. The method as claimed in claim 1, wherein the mixture is prepared by adding each of components (a)-(d), and subsequently, in the presence of the polyglycerol-3, the simultaneous transesterification is performed on the mixture, and wherein, prior to commencing the simultaneous transesterification, the mixture is an unreacted mixture.

* * * * *